United States Patent [19]
Mischenko

[11] Patent Number: 5,374,239
[45] Date of Patent: Dec. 20, 1994

[54] ARTERIAL SHUNT WITH BLOOD FLOW INDICATOR

[75] Inventor: Peter S. Mischenko, Mount Prospect, Ill.

[73] Assignee: Metatech Corporation, Wheeling, Ill.

[21] Appl. No.: 925,393

[22] Filed: Aug. 4, 1992

[51] Int. Cl.$^5$ .............................................. A61M 1/00
[52] U.S. Cl. .......................................... 604/8; 604/96; 604/100
[58] Field of Search .................. 604/8, 9, 93, 96, 100, 604/104, 118; 137/559; 116/273, 274

[56] References Cited

U.S. PATENT DOCUMENTS

| | | | |
|---|---|---|---|
| 2,867,213 | 1/1959 | Thomas, Jr. | 137/559 |
| 3,185,128 | 5/1965 | Moore et al. | 116/274 |
| 4,101,874 | 7/1978 | Denison et al. | 116/274 X |
| 4,559,034 | 12/1985 | Kirita et al. | 604/118 X |
| 4,712,551 | 12/1987 | Rayhanabad | 604/8 X |
| 4,745,877 | 5/1988 | Chang | 116/273 X |
| 4,793,190 | 12/1988 | Chang | 116/274 X |
| 4,872,483 | 10/1989 | Shah | 604/100 X |
| 5,030,227 | 7/1991 | Rosenbluth et al. | 604/96 X |

*Primary Examiner*—Sam Rimell

[57] ABSTRACT

An arterial shunt is disclosed having means for indicating the flow of blood through the shunt. The shunt comprises a movable indicator element responsive to the flow of blood. Whether or not blood is flowing through the shunt may be quickly and easily ascertained by visual inspection of the indicator element through a transparent window. Alternatively, electromagnetic or optical means may be employed to measure the velocity of the movement of the indicator element which also allows the rate of blood flow through the shunt to be quantified.

10 Claims, 3 Drawing Sheets

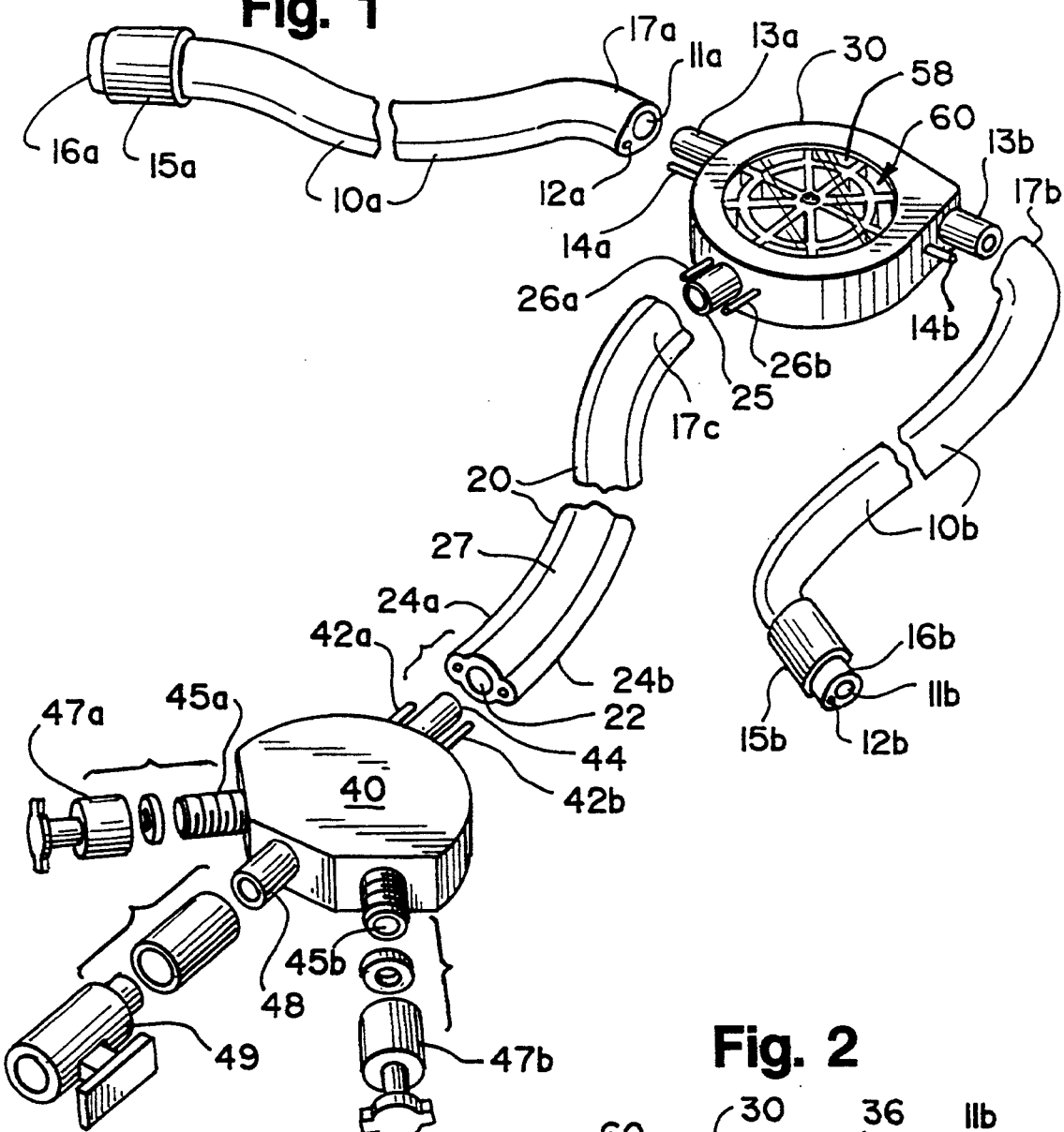
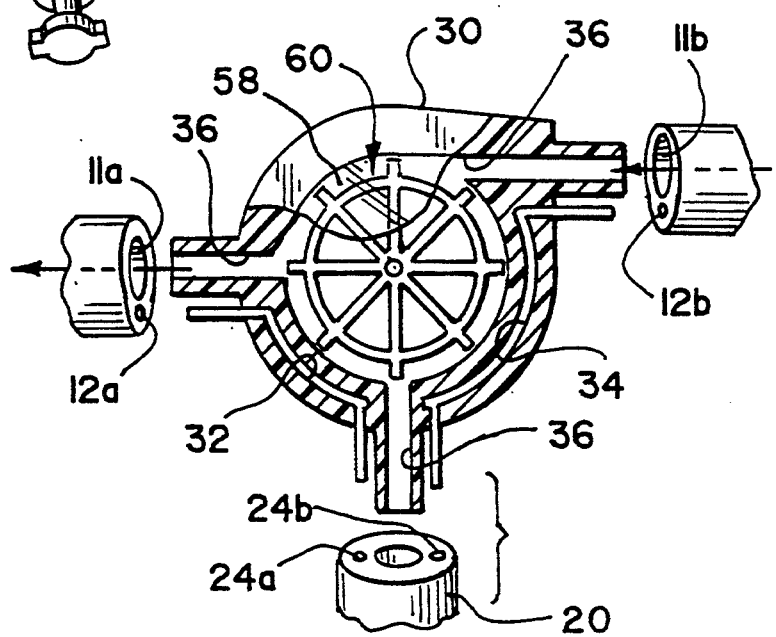
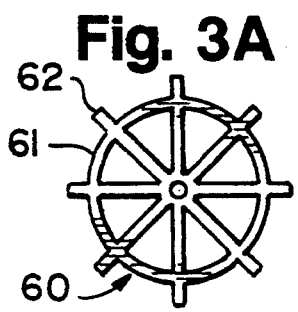
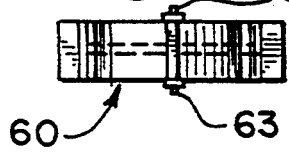

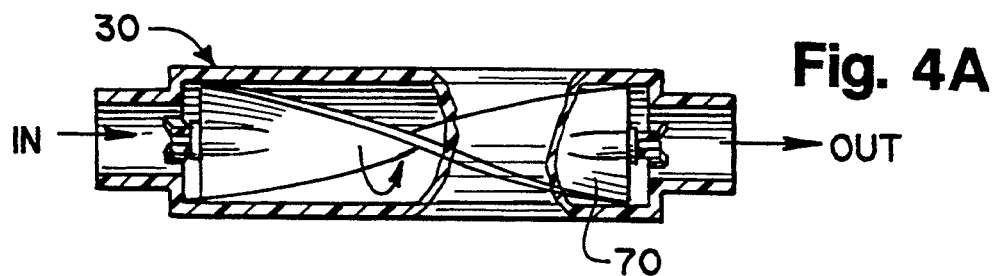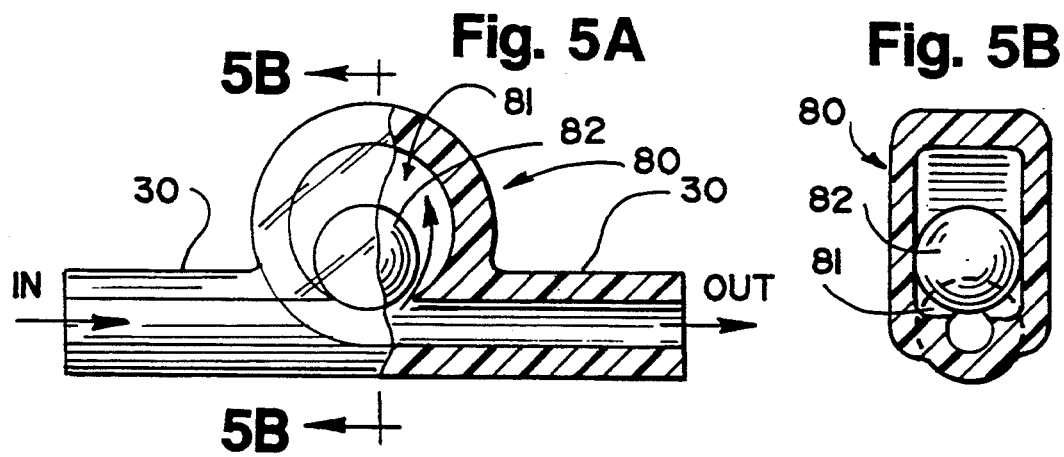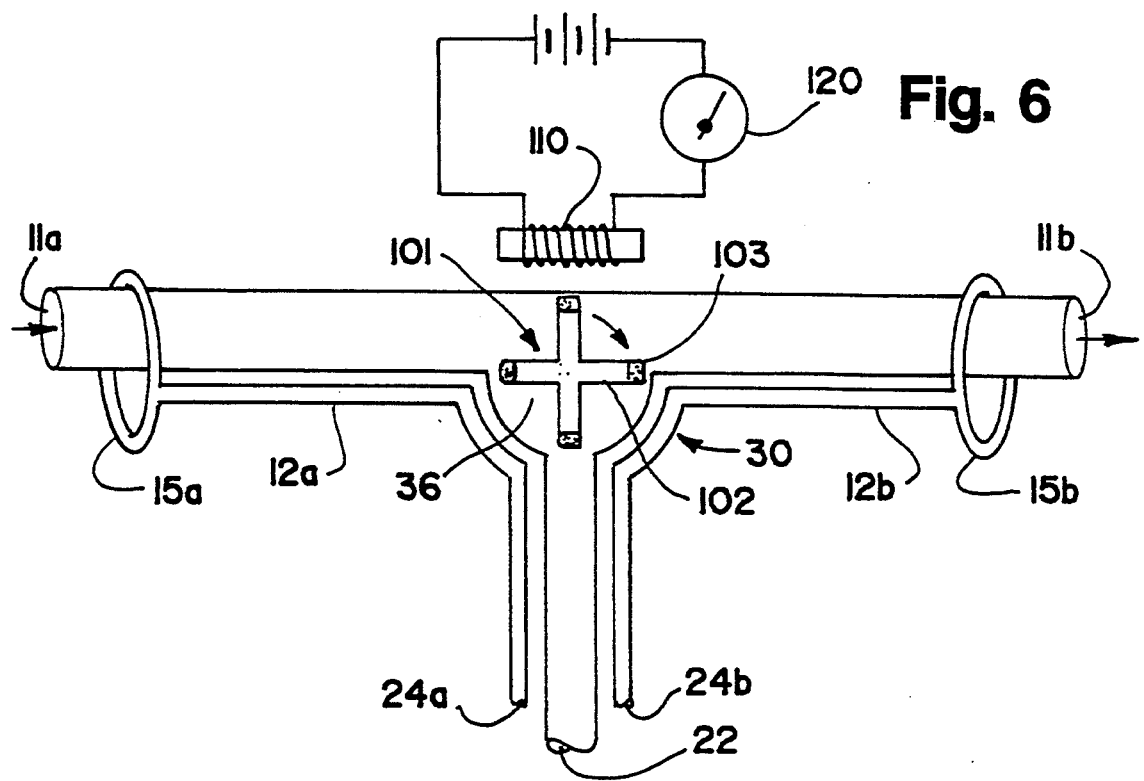

ARTERIAL SHUNT WITH BLOOD FLOW INDICATOR

BACKGROUND

Occlusive disease of an artery, frequently the result of atherosclerosis, is sometimes treated by the surgical procedure of endarterectomy. In an endarterectomy, an incision is made in the artery at the site of the occlusion. The thickened intima of the artery along with any other components of the lesion such as atherosclerotic plaque or thrombus, is then removed. In order to perform this procedure, the artery must necessarily be occluded above and below the area operated upon, typically with a pair of clamps. This means that there is no blood flow through the artery during the operation, but collateral circulation is usually adequate to support the metabolism of the area fed by the artery for a short period.

One of the most common sites of occlusive arterial disease is the internal carotid artery, usually at its origin at the bifurcation of the common carotid. Endarterectomy is sometimes the treatment of choice for these cases. Clamping of the carotid artery as described above, however, necessarily means that cerebral blood flow is compromised during the procedure. The situation can be evaluated during the operation by measuring the pressure in the internal carotid artery after application of occluding vascular clamps to the common carotid artery and the external carotid artery. This measurement of carotid "stump pressure" is indicative of the adequacy of collateral circulation to the brain. If it is below 50 mmHg, brain perfusion may not be adequate, thus necessitating the use of a temporary shunt during the procedure. Some surgeons even choose to routinely use such a shunt during all carotid endarterectomies without regard to measured "stump pressure."

An arterial shunt is basically a pliable tube which provides a pathway through which blood may flow in order to bypass the operative site. A conventional shunt is formed with two limb sections joined together with a single trunk section extending from the point where the two limbs meet. A continuous blood flow lumen exists in all three sections. One limb is inserted into the artery through the surgical incision on one side of the lesion while the other limb is inserted on the opposite side of the lesion. Blood then flows from one limb to the other, thus bypassing the operative site. The trunk section is normally connected to a stopcock which allows access to the circulation for pressure monitoring or drug administration, as well as allowing air in the shunt to be purged. The trunk section also contains two auxiliary lumena separate from the blood flow lumen. Each auxiliary lumen extends into a selective one of the limb sections. At the distal end of each limb, an annular balloon is positioned which surrounds the shunt tubing but does not obstruct the blood flow conduit. Each annular balloon is connected to an auxiliary lumen from which the balloon may be inflated, typically with saline. Thus, a tight seal is formed within the artery to provide an effective bypass and to keep the operative field free of blood. Alternatively, the auxiliary lumena and balloon arrangement may be eliminated and replaced by simply tying a suture around the artery to secure the limb section within on each side of the incision.

A major complication which can arise while performing a shunt endarterectomy is for the shunt to become occluded either by a thrombus or dislodged plaque. This can occur initially as the shunt is inserted into the artery or at any time during the procedure. This is, of course, a potentially disastrous complication unless corrective action is taken quickly. However, in heretofore conventional shunts it has been difficult to tell whether blood is flowing adequately therethrough.

SUMMARY OF THE INVENTION

It is a primary object of the present invention to provide an arterial shunt having means by which the operability of the shunt can be easily and continuously monitored.

The present invention provides an arterial shunt comprising two limb sections and a trunk section, each section made of pliable tubing and having a blood flow lumen integral thereto. In a preferred embodiment, an auxiliary lumen also is provided integral to each limb section for inflating an annular balloon surrounding the distal end of each limb in order to provide a tight seal against the arterial wall. The trunk section has integral thereto two separate auxiliary lumena, each corresponding to one of the limb auxiliary lumena. The shunt further comprises an indicator housing coupled to the trunk and each limb section. Within the indicator housing are three separate flow pathways. Two of the three pathways establish separate fluid communication between each limb auxiliary lumen and its corresponding trunk auxiliary lumen. The other pathway establishes fluid communication between the blood flow lumena of both limbs and the trunk. Interposed within the blood flow pathway of the indicator housing is a flow indicator element which is movable responsive to the flow of fluid through the pathway. A transparent window provided in the shunt allows visual inspection of the position or movement of the indicator element in order to monitor the flow of blood from one limb to the other.

In another embodiment, the flow of blood through the indicator housing may be indicated by electromagnetic means which also allows the blood flow to be quantified. In accordance with this aspect of the invention, a magnetic element is formed on an indicator element which rotates in response to blood flow. An inductor is positioned relative to the indicator element so as to receive flux from the magnetic element, the flux varying according to the position of the indicator element. An A.C. voltage is thereby generated in the inductor whose magnitude and frequency are functions of the angular velocity of movement of the indicator element, the latter quantity being proportional to the velocity of blood flowing through the indicator housing. The inductor voltage is thus a function of the rate of blood flow through the shunt.

In accordance with a further embodiment of the present invention, the velocity of movement of the magnetic indicator element may also be measured for purposes of determining blood flow and the rate thereof by using a Hall-effect sensor to produce voltage pulses at a frequency proportional to the indicator element's angular velocity. Optical means may also be employed for the same purpose using an optical transmitter/sensor where the transmission of a light beam is affected by portions of a rotating indicator element which may be either opaque or reflective.

Other objects, features, and advantages of the invention will become evident in light of the following detailed description considered in conjunction with the referenced drawings of a preferred exemplary embodiment according to the present invention.

BRIEF DESCRIPTION OF THE DRAWINGS

FIG. 1 shows the components of an arterial shunt in accordance with the present invention.

FIG. 2 shows a detailed view of the indicator housing shown in FIG. 1.

FIGS. 3A-B, 4A-B, and 5A-B show alternative embodiments of the flow indicator element.

FIG. 6 shows an alternative embodiment for quantifying blood flow.

DETAILED DESCRIPTION OF THE INVENTION

Figure 7:
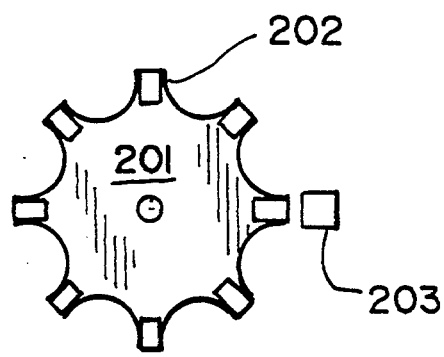
FIGS. 7, 8, and 9A-B show other alternative embodiments for quantifying blood flow.

FIG. 1 shows an embodiment of the present invention in a disassembled state. Limb sections 10a and 10b are constructed of pliable tubing material such as silicone, as is trunk section 20. Each of the limbs 10a, 10b has a separate blood flow lumen, 11a, 11b, respectively, integral thereto which extends continuously from one end of the limb to the other. Each limb 10a, 10b also has therein a separate auxiliary lumen, 12a, 12b, respectively, which is open at its proximal end and which communicates with an annular balloon 15a, 15b, respectively, surrounding its distal end. Auxiliary lumena 12a, 12b are employed to inflate the balloons 15a, 15b so as to form a sealing cuff against the arterial walls (not shown) after insertion of the distal ends 16a, 16b of the limbs into the lumen of an artery. Within trunk section 20 are a single blood flow lumen 22 and auxiliary lumena 24a and 24b which run continuously from end to end.

The limb sections 10a, 10b and the trunk section 20 have their proximal ends 17a, 17b, 17c, respectively, coupled to an indicator housing 30. The lumena 11a, 12a, 11b, 12b of limb sections 10a and 10b are sealingly fit over nipple extensions 13a, 14a and 13b, 14b, respectively, while the lumena 22, 24a, 24b of trunk 20 are fit over nipple extensions 25, 26a, and 26b, respectively. As illustrated in FIG. 2, separate auxiliary pathways exist inside indicator housing 30 such that fluid communication is established between trunk auxiliary lumen 24a and limb auxiliary lumen 12a via auxiliary pathway 32 and between trunk auxiliary lumen 24b and limb auxiliary lumen 12b via auxiliary pathway 34. The balloons 15a, 15b thus may be inflated or deflated with saline via the auxiliary lumena 24a, 24b of trunk section 20. Another separate blood flow pathway 36 exists inside indicator housing 30 such that fluid communication is established between blood flow lumena 11a, 11b, and 22.

In order to provide a bypass pathway, the distal end 27 of trunk 20 can be either connected to a valve or clamped off so that the blood flow from one limb to the other through the separate blood flow pathway 36 inside the indicator housing 30 can be redirected out through such valve or clamp assembly. In order to prevent blood flowing through pathway 36 in indicator housing 30 from being unintentionally siphoned off through trunk 20, a valve or clamp assembly (not shown) may be applied to the distal end of trunk 20 thereby maintaining unobstructed blood flow from one limb to the other. However, in certain instances, it may be desirable to couple the trunk 20 to a terminal housing 40 as shown in FIG. 1. Terminal housing 40 has separate nipple extensions 42a, 42b and 44 over which the auxiliary lumena 24a, 24b and blood flow lumena 22, respectively, of trunk 20 are fit. Separate flow pathways (not shown) are provided inside the terminal housing 40 for each lumen, the pathway being similar to the pathways 32, 34 and 36 formed in indicator housing 30, as described above. Each auxiliary pathway in housing 40 is continuous with a separate tap 45a or 45b which is coupled to a valve assembly 47a or 47b, respectively. Saline can thus be injected or withdrawn through valve assemblies 47a, 47b to control the inflation of balloons 15a, 15b, respectively. The blood flow pathway inside housing 40 is continuous with tap 48 which is coupled to a valve assembly 49. Valve assembly 49 is closed to provide a limb to limb bypass pathway but can be opened to allow access to circulation.

As shown in FIGS. 2 and 3A-B, a movable flow indicator element 60 is interposed within the blood flow pathway within the indicator housing 30. This flow indicator element 60 is positioned and structured to move in response to the flow of blood within the blood pathway 36. At least a portion of the indicator housing 30 is formed with a transparent opening to provide a window 58 for visual inspection of the indicator element 60. In the embodiment illustrated in FIGS. 3A and 3B, element 60 is a wheel 61 having radially extending fins 62 and rotatably mounted within the housing 30 by means of axles 63 oriented perpendicularly to the direction of blood flow. As shown in FIG. 2, the blood flow pathways inside the housing 30 are constructed such that blood is constrained to flow tangentially to wheel 61 which thus causes the indicator 60 to rotate. Different sections of the indicator 60 may be painted with contrasting colors to enhance visibility of its rotation. In this manner, blood flow through the shunt may be easily and continuously monitored.

FIGS. 4A-B show an embodiment of a flow indicator 70 which comprises a finned body 72 having a shaft 71 for mounting the indicator 70 rotatably within the indicator housing 30 coaxial to the direction of blood flow. Fins 72 are canted such that flow through the housing 30 causes the indicator 70 to rotate in one direction or the other as shown by an arrow in FIG. 4A. Again, rotation of element 70, which may be more easily observed if it is painted with interspersed contrasting colors, indicates that blood is flowing through the shunt.

FIGS. 5A-B shows an embodiment of a flow indicator element 80 comprising a compartment 81 within which is situated a ball 82 freely movable within the compartment. Compartment 81 communicates with the blood flow pathway of the indicator housing through an opening 83 which is small enough so that ball 82 remains contained. Blood flowing past the opening 83, especially if it is pulsatile, causes turbulence within the compartment 81. Such turbulence causes observable movement of ball 82 to indicate blood flow. Many other embodiments of visible flow indicator elements are possible, of course, which utilize a movable element which responds to flow by moving or changing position.

The embodiments described above all allow the determination by visual inspection of whether blood is flowing through the shunt or not. In certain applications, however, it may be useful to demonstrate blood flow by non-visual means as well as to quantify the rate of blood flow. Accordingly, illustrated in FIG. 6 is an alternative embodiment of the present invention. Flow element 101 is a wheel having radially extending fins 102 mounted within the indicator housing 30 so as to be freely rotatable, similar to element 60 as shown in FIGS. 2 and 3A-B. Element 101 is thus caused to rotate by blood flowing through the housing 30 within the blood flow pathway 36. The angular velocity of flow element 101 will be proportional to the velocity of the blood flow through pathway 36 if frictional effects are minimized. Thus, by measuring the number of rotations per minute made by flow element 101, one can calculate with a proportionality factor the velocity of the blood flowing through the indicator housing. Since the volumetric flow rate of a fluid within a rigid conduit is equal to the velocity of the fluid times the cross-sectional area of the conduit, the rate of blood flow through the indicator housing 30 may be calculated by multiplying the velocity of the blood flow by another proportionality constant equal to the cross-sectional area of the blood flow pathway 36 in which is interposed flow element 101. Thus, the blood flow through the shunt may be quantified by multiplying the angular velocity of element 101 by a suitable constant.

It is desirable, of course, to sense the angular velocity of element 101 without wires or other physical structures passing from element 101 to the outside which creates sealing and sterility problems. In accordance with the present invention, therefore, electromagnetic means are employed for this purpose. As shown in FIG. 6, a magnetic material is embedded in the tips 103 of fins 102 on flow element 101. Preferably, at least two opposite fins should have magnetic tips so that the element 101 remains balanced. A magnetic inductor 110 is placed in proximity to the flow element 101 so that it receives magnetic flux from the rotating magnetic tips 103. An A.C. voltage is thus induced in the inductor 110 which is proportional to the rate of change of magnetic flux through its coils which, in turn, is proportional to the angular velocity of element 101. The inductor 110 generates a voltage within an external circuit which includes an ampmeter 120. The measured current, after appropriate scaling, thus represents the rate of blood flow through the shunt.

Other techniques may also be used to indicate blood flow and to measure the velocity of movement of the flow indicator element. For example, rather than using an inductor, a Hall-effect sensor can be used to sense the magnetic field produced by the indicator's magnetic element. Such an embodiment is shown in FIG. 7 where indicator element 201 having fins with magnetic tips 202 is mounted in a freely rotatable manner within an indicator housing (not shown) in communication with blood flowing through a blood flow pathway (not shown) similar to pathway 36, best illustrated in FIGS. 2, 3A-B and 6, so that, as the indicator rotates, a Hall-effect sensor 203 produces a voltage pulse whenever one of the magnetically tipped fins comes into the proximity of the sensor. The frequency of the pulses thereby produced is proportional to the angular velocity of the indicator element 201.

Figure 8:
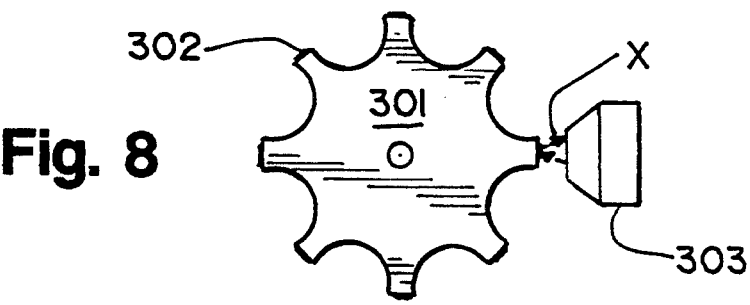

FIG. 8 shows another embodiment of the present invention utilizing an optical technique for measuring the angular velocity of an indicator element 301 mounted in a housing (not shown) in a manner similar to the indicators depicted elsewhere herein. In this embodiment the tips of fins 302 of element 301 are made reflective, and an optical sensor/transmitter 303 is positioned adjacent the indicator 301. Thus, in operation, as a reflectively tipped fin 302 is rotated to a position opposite the transmitter/sensor 303, a light beam (x) is transmitted from the transmitter/sensor 303 onto the reflective surface of the reflective tipped fin 303. The beam is reflected back to the transmitter/sensor so as to cause a voltage pulse. Again, the frequency of the voltage pulses is proportional to the flow indicator element's angular velocity.

Figure 9A:
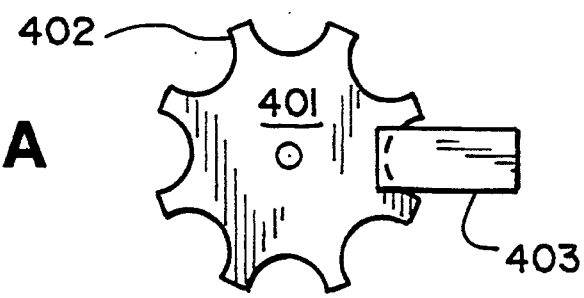
Figure 9B:
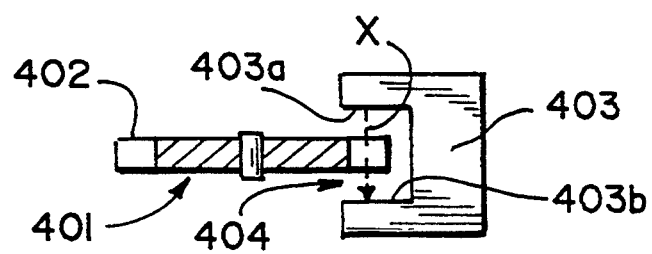

Yet another technique for measuring the angular velocity of the flow indicator element is represented in FIGS. 9A–B. In this embodiment, an optical transmitter/sensor 403 has its sensor 403a and transmitter 403b separated by a gap 404 so that a light beam (x) emitted from transmitter 403b traverses the gap to reach the sensor 403a. The transmitter/sensor 403 is positioned adjacent a rotating indicator element 401 having opaque fins 402. The indicator element 401 is mounted in a housing (not shown) in a manner similar to the other indicators illustrated herein and is positioned so that the indicator 401, along with the surrounding indicator housing, lies within the gap 404. When the position of element 401 is such that one of its opaque fins 402 obstructs the optical pathway from transmitter 403b to sensor 403a, the light beam traveling through transparent windows of the indicator housing is interrupted so that no voltage is produced by the sensor. When element 401 rotates so that the light beam path is unobstructed, a voltage pulse is produced. The measured frequency of the pulses, as before, is proportional to the angular velocity of element 401.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. An arterial shunt comprising:
    a pair of pliable limb sections with each section having a separate blood flow lumen integral thereto;
    a pliable trunk section having a blood flow lumen integral thereto;
    an indicator housing connected to the trunk and both limb sections and having a blood flow pathway therein for establishing communication between the blood flow lumena of the trunk and both limb sections; and
    a flow indicator element interposed within the blood flow pathway of the indicator housing, said indicator being movable responsive to blood flow within the pathway enabling monitoring of the continuing flow of blood therein.

2. The arterial shunt as set forth in claim 1 wherein the movement of said flow indicator element provides a visual indication of the continuing blood flow.

3. The arterial shunt as set forth in claim 2 further comprising a window formed in the indicator housing through which the flow indicator element is viewable.

4. The arterial shunt as set forth in claim 3 wherein the flow indicator is a wheel rotatably mounted within the indicator housing by means of axles oriented perpendicularly to the direction of blood flow and having radially extending fins such that blood flow through the housing causes rotation of the wheel.

5. An arterial shunt comprising:
    a pair of limb sections with each section having a separate blood flow lumen integral thereto;
    a trunk section having blood flow and auxiliary lumena integral thereto;
    an indicator housing connected to the trunk and both limb sections and having a blood flow pathway therein for establishing communication between the blood flow lumena of the trunk and both limb sections;

a flow indicator element interposed within the blood flow pathway of the indicator housing, said indicator being movable responsive to blood flow within the pathway enabling monitoring of the continuing flow of blood therein;

auxiliary lumena formed integral to said limb sections and said trunk section;

an auxiliary pathway in the indicator housing connected to each auxiliary lumena in said limbs and said trunk to establish fluid communication between said auxiliary lumena; and annular balloons surrounding the distal end of each limb section and connected to the auxiliary lumen of said limb sections in a manner such that said balloons may be inflated to seal an artery upon insertion therein.

6. The arterial shunt as set forth in claim 5 further comprising a terminal housing connected to the trunk section and having separate blood flow pathway and outflow taps for the trunk auxiliary and blood flow lumena.

7. An arterial shunt comprising:

a pair of limb sections made of pliable tubing with each section having separate blood flow and auxiliary lumena integral thereto;

a trunk section made of pliable tubing having integral thereto a blood flow lumen and an auxiliary lumen corresponding to each limb auxiliary lumen;

an annular balloon surrounding the distal end of each limb section and connected to the limb auxiliary lumen;

an indicator housing connected to the trunk and both limb sections and having a separate blood flow and auxiliary pathways herein for establishing fluid communication between each limb auxiliary lumen and its corresponding trunk auxiliary lumen and between the blood flow lumena of the trunk and both limb sections; and, a movable flow indicator element within the blood flow pathway of the indicator housing responsive to fluid flow to enable monitoring of the blood flow therein.

8. The arterial shunt as set forth in claim 7 wherein the movement of said flow indicator element provides a visual indication of the continuing blood flow.

9. The arterial shunt as set forth in claim 8 further comprising a window formed in the indicator housing through which the flow indicator element is viewable.

10. The arterial shunt as set forth in claim 7 wherein the flow indicator is a wheel rotatably mounted within the indicator housing by means of axles oriented perpendicularly to the direction of blood flow and having radially extending fins such that blood flow through the housing causes rotation of the wheel.

* * * * *